United States Patent
Clough et al.

(10) Patent No.: US 12,029,241 B2
(45) Date of Patent: Jul. 9, 2024

(54) ELECTRONIC CIGARETTE WITH PROTECTIVE COVER

(71) Applicant: JT International S.A., Geneva (CH)

(72) Inventors: Richard Brian Clough, Stourbridge (GB); Aled James, Dorridge (GB); Kyle Adair, Lisburn (GB)

(73) Assignee: JT International S.A. (CH)

( * ) Notice: Subject to any disclaimer, the term of this patent is extended or adjusted under 35 U.S.C. 154(b) by 904 days.

(21) Appl. No.: 17/044,603

(22) PCT Filed: Apr. 24, 2019

(86) PCT No.: PCT/EP2019/060434
§ 371 (c)(1),
(2) Date: Oct. 1, 2020

(87) PCT Pub. No.: WO2019/206943
PCT Pub. Date: Oct. 31, 2019

(65) Prior Publication Data
US 2021/0022399 A1 Jan. 28, 2021

(30) Foreign Application Priority Data
Apr. 24, 2018 (EP) .................................... 18169013

(51) Int. Cl.
*A24F 13/14* (2006.01)
*A24F 40/40* (2020.01)
(Continued)

(52) U.S. Cl.
CPC .............. *A24F 13/14* (2013.01); *A24F 40/40* (2020.01); *A24F 40/42* (2020.01); *A24F 40/10* (2020.01); *A24F 40/60* (2020.01)

(58) Field of Classification Search
None
See application file for complete search history.

(56) References Cited

U.S. PATENT DOCUMENTS 9,549,573 B2 * 1/2017 Monsees .................. H05B 3/04
2008/0241255 A1 * 10/2008 Rose ....................... A24F 42/20
514/343

(Continued)

FOREIGN PATENT DOCUMENTS

| CN | 204157645 U | 2/2015 |
| CN | 107734983 A | 2/2018 |

(Continued)

OTHER PUBLICATIONS

Extended European Search Report including Written Opinion for Application No. EP18169013.2, dated Oct. 11, 2018, pp. 1-8.

(Continued)

*Primary Examiner* — Tho D Ta
(74) *Attorney, Agent, or Firm* — Lerner David LLP

(57) ABSTRACT

An electronic cigarette device includes an elongate main body including a power supply unit, electrical circuitry and a seating for a liquid reservoir. Front and back panels are slidably attached to the elongate main body and configured to move in the longitudinal direction between an extended position and a retracted position. The panels include connectors configured to slide on rail members in a longitudinal direction. The connectors include a movable portion that is movable relative to a fixed portion, and which allows movement of the panel in a direction that is transverse to the longitudinal axis of the rail members.

18 Claims, 8 Drawing Sheets

(51) Int. Cl.
  *A24F 40/42* (2020.01)
  *A24F 40/10* (2020.01)
  *A24F 40/60* (2020.01)

(56) References Cited

U.S. PATENT DOCUMENTS

| | | | |
|---|---|---|---|
| 2014/0366898 A1 | 12/2014 | Monsees et al. | |
| 2015/0272211 A1* | 10/2015 | Chung | A24F 40/40 |
| | | | 206/242 |
| 2017/0302324 A1* | 10/2017 | Stanimirovic | H04M 1/185 |
| 2018/0177234 A1 | 6/2018 | Lee | |
| 2018/0360125 A1* | 12/2018 | James | A24F 40/40 |
| 2021/0059305 A1* | 3/2021 | Clough | A24F 40/40 |
| 2023/0082657 A1* | 3/2023 | James | A24F 40/60 |
| | | | 131/273 |

FOREIGN PATENT DOCUMENTS

| | | | | |
|---|---|---|---|---|
| KR | 20170006282 A | 1/2017 | | |
| TW | 201724976 A | 7/2017 | | |
| WO | 20177252 A1 | 1/2017 | | |
| WO | WO-2017007252 A1 * | 1/2017 | ........... | A24B 15/167 |
| WO | 2017102969 A1 | 6/2017 | | |

OTHER PUBLICATIONS

International Search Report including Written Opinion for Application No. PCT/EP2019/060434, dated Jul. 22, 2019, pp. 1-11.
Search Report dated Mar. 14, 2023 from the Office Action for Chinese Application No. 201980027872.8 dated Mar. 20, 2023, pp. 1-2. [See p. 1, categorizing the cited references].

* cited by examiner

ELECTRONIC CIGARETTE WITH PROTECTIVE COVER

CROSS-REFERENCE TO RELATED APPLICATIONS

The present application is a national phase entry under 35 U.S.C. § 371 of International Application No. PCT/EP2019/060434, filed Apr. 24, 2019, published in English, which claims priority to European Application No. 18169013.2 filed Apr. 24, 2018, the disclosures of which are incorporated herein by reference.

BACKGROUND AND PROBLEMS SUMMARY

Field of Invention

The present invention relates to personal vaporizing devices, such as electronic cigarettes.

Background

Electronic cigarettes are an alternative to conventional cigarettes. Instead of generating a combustion smoke, they vaporize a liquid, which can be inhaled by a user as an aerosol. The liquid typically comprises an aerosol-forming substance, such as glycerin or propylene glycol that creates the vapor. Other common substances in the liquid are nicotine and various flavorings.

The electronic cigarette is a hand-held inhaler system, comprising a mouthpiece, a liquid reservoir, a vaporizer or heating unit and a power supply unit. Vaporisation occurs when the heating unit heats up the liquid to a temperature exceeding the boiling temperature of the liquid. The liquid reservoir can be configured as a refillable reservoir. Alternatively, the electronic cigarette may comprise a capsule seating that is configured to receive disposable consumables in the form of capsules.

Electronic cigarettes are used several times and often carried around in pockets or handbags. It is therefore desirable to protect the mouthpiece and keep it clean to avoid dirt and debris from attaching to the mouthpiece.

WO 2017/102969 discloses a slideable protection cover for an electronic cigarette. The electronic cigarette in WO 2017/102969 comprises a pair of slideable panels, which are moveable to either cover or expose the mouthpiece of the electronic cigarette.

SUMMARY

It is an object of the present invention to further improve the slideable protection of the prior art. A further object is to improve indicators with which such an electronic cigarette can communicate information to a user.

According to a first aspect of the present invention, it relates to an electronic cigarette device comprising:
  an elongate main body configured to house a liquid reservoir,
  at least one slideable panel connected to the elongate main body and moveable in relation to the main body in a longitudinal direction of the elongate main body between an extended position and a retracted position, whereby the liquid reservoir is exposed or more exposed when the panel is in the retracted position,
  wherein one of the elongate main body and the panel comprises at least one guide member and the other of the elongate main body and the panel comprises at least one connector configured to connect to the at least one guide member,
  and wherein the at least one connector is connected to the at least one guide member such that the panel is slideably moveable relative to the elongate main body in the longitudinal direction and is also movable in a transverse direction that is perpendicular to the longitudinal direction.

According to an exemplary embodiment, the elongate main body comprises the at least one guide member and the panel comprises the at least one connector.

According to an exemplary embodiment, the liquid reservoir is configured as a removable capsule provided with a mouthpiece portion. In another embodiment, the liquid reservoir may be configured as a permanent and refillable tank.

In an embodiment, the at least one connector is biased in the transverse direction. A deformable biasing member is preferably provided. The deformable biasing member preferably allows movement of the panel in the transverse direction, and provides a restoring force towards a stable position.

The at least one connector may comprise a fixed portion fixedly attached to the panel and a moveable portion that is movable in relation to the fixed portion in the transverse direction.

The fixed portion may comprise first and second protrusions, wherein the movable portion is slidably received between the first and second protrusions.

The at least one connector preferably comprises a keyway configured to receive the guide member.

In an embodiment, the keyway comprises a first contact surface on one side of the guide member and a second contact surface on the other side of the guide member, wherein at least one of the first contact surface and the second contact surface is biased towards the guide member.

The first and second contact surfaces are preferably made from nylon, polyester or Teflon.

The connector comprises a biasing member configured to bias the movable portion relative to the fixed portion. The biasing member is preferably a resilient material. The resilient material may comprise a spongy foam such as polyurethane or polyethylene.

In an exemplary embodiment, the panel is arranged to move at a distance of between 0.05 and 1 mm in the transverse direction of the main body.

In an exemplary embodiment, the electronic cigarette further comprises a second slideable panel configured to move in unison with the first slideable panel.

In an exemplary embodiment, the at least one connector of the first panel is in abutment with at least one connectors of the second panel such that they move together. The first panel is preferably configured as a front panel and the second panel is preferably configured as a back panel.

According to an exemplary embodiment, the main body comprises an electrical activation circuit and actuator element,
  wherein the panel comprises an engagement element configured to move the actuator element, whereby the electrical activation circuit is only activated when the at least one panel is in the retracted position.

The activation circuit may be located on a printed circuit board (PCB).

In an exemplary embodiment, wherein the panel further comprises a heating element activation button and wherein the activation button is only operable when the panel is in the retracted position. The main body preferably has at least one abutment portion configured to protect the PCB from the activation button when the panel is in an extended position.

The front panel preferably comprises a user-interface and the elongate main body preferably comprises at least one light source. The front panel preferably comprises at least one light-diffusing portion configured to be illuminated by the light sources when the light sources are aligned with the light-diffusing portions.

The light source may be a LED, preferably a RGB. The light source may be connected to the illumination areas of the display via a light guide.

According to other aspects, the present concept also relates to an electronic cigarette device comprising:
- an elongate main body configured to receive a liquid store,
- at least one slideable panel connected to the elongate main body and movable in the longitudinal direction of the electronic cigarette between an extended position and a retracted position, whereby the liquid store is exposed or more exposed when the panel is in the retracted position,
- a first light source that is configured to be rendered operable when the panel is in the retracted position, and that is configured to be rendered inoperable or invisible when the panel is in the extended position.

As the slidable panel is configured to move in relation to the main body, there is a greater need for providing light to illuminate the display when the slidable cover is in a retracted position and the electronic cigarette is activated. When the electronic cigarette is turned off and the panel is in an extended position, there is a reduced need for illuminating the display.

The present configuration of the lights and the slidable cover provides for extended battery life as the main display is only illuminated when the electronic cigarette is activated. However, some functions, like the battery charging function can be used in both the extended and retracted positions of the slidable panel. The display functions in the non-activated position may be provided by less light sources. Because the battery charging status should be visible in both the extended and the retracted position, it is possible to create a simple configuration with two sets of light sources that can either be individually or jointly operated. If the light sources are jointly operated, only one of the light sources or group of light sources are visible at a time as one of them will be illuminated under the non-transparent portions of the slidable panel.

According to an exemplary embodiment, the first light source may be provided on the elongate main body and wherein the panel comprises a translucent portion configured to be aligned with the first light source only when the panel is in the retracted position so that light from the first light source is visible through the translucent portion when the panel is in the retracted position.

The elongate main body may further comprise a second light source which is aligned with the translucent portion only when the panel is in the extended position so that light from the second light source is visible through the translucent portion when the panel is in the extended position.

In an exemplary embodiment, the first light source comprises a plurality of light emitting elements and each element is aligned with a respective translucent portion only when the panel is in the retracted position. The respective translucent portions may be divided from one another by optically opaque partitions.

According to an exemplary embodiment, the light sources are electrically connected to a printed circuit board, PCB.

According to an exemplary embodiment, the electronic cigarette further comprises at least one light diffuser configured to receive and diffuse light from the first light source.

According to an exemplary embodiment, the electronic cigarette may comprise a switch configured to render operable the main power circuit of the electronic cigarette.

According to an exemplary embodiment, the at least one slideable panel comprises an actuator configured to activate a switch on the elongate main body to control a power supply between an operable state and an inoperable state when the panel is in the retracted and extended positions, respectively.

According to an exemplary embodiment, the slideable panel comprises a press-button that can activate a switch on the elongate main body to enable the production of inhalable aerosol.

According to an exemplary embodiment, the press-button is movable from a first position towards a second position that is closer to the main body, and wherein movement of the press-button from the first position towards the second position is inhibited when the slideable panel is in the extended position.

According to an exemplary embodiment, the elongate main body comprises at least one abutment, configured to inhibit movement of the press-button from the first position toward the second position.

According to an exemplary embodiment, the abutment forms part of a light diffuser. According to an exemplary embodiment, the at least one light source is illuminated when the actuator is activated.

According to an exemplary embodiment, the at least one light source is illuminated when the electronic cigarette is connected to an external device via a socket.

According to an exemplary embodiment, the external device is a charger.

According to an exemplary embodiment, the electronic cigarette further comprises a wireless signal receiver and wherein the at least one light source is configured to be illuminated when the electronic cigarette receives a wireless signal from an external device.

According to an exemplary embodiment, the external device is a portable computing device such as a smartphone.

According to an exemplary embodiment, the light sources are pulsed at different intervals to indicate different types of information.

According to an exemplary embodiment, the liquid store is configured as a removable and disposable capsule and wherein the main body further comprises a capsule seating configured to receive replaceable capsules comprising a liquid store.

According to an exemplary embodiment, the liquid store is refillable.

According to an exemplary embodiment, wherein the main body further comprises an electronic memory configured to store capsule parameters.

According to an exemplary embodiment, the main body further comprises a controller and a sensor, and wherein the controller is configured to change the color of the light source based on sensed information from the sensor or from calculated information from the controller.

According to an exemplary embodiment, the sensor is a voltage sensor.

According to an exemplary embodiment, the controller is configured to change color of the light source based on information from the controller such as a total estimated consumption, duration of utilization, remaining battery power or capsule information.

According to an exemplary embodiment, the controller is configured to retrieve information from the change color of the light source based on product information selected from the group comprising authentication information, expiry date and chemical composition (e.g. nicotine content).

According to an exemplary embodiment, the main body further comprises a second group of light sources, wherein the second group of light sources is selectively activated by a switch when the panel is in the extended position.

According to a further aspect of the present concept, it relates to an electronic cigarette device comprising:
  an elongate main body configured to receive a liquid store,
  at least one slideable panel connected to the elongate main body and movable in the longitudinal direction of the electronic cigarette between an extended position and a retracted position, whereby the liquid store is exposed or more exposed when the panel is in the retracted position, the panel comprising at least one actuator button,
  wherein the elongate main body comprises a switch that can be actuated by the actuator button, and wherein the button is movable from a first position towards a second position that is closer to the main body and in which it can actuate the switch, and wherein movement of the button from the first position towards the second position is inhibited when the slideable panel is in the extended position.

According to an exemplary embodiment, the elongate main body comprises a printed circuit board on which the switch is mounted and an abutment, wherein the button is positioned in registry with the abutment when the slideable panel is in the extended position to inhibit movement of the button from the first position towards the second position.

According to an exemplary embodiment, the electronic cigarette further comprises a first light source electrically connected to the printed circuit board and a light diffuser arranged between the slideable panel and the first light source.

According to an exemplary embodiment, the light sources are pulsed at different intervals to indicate different types of information.

According to an exemplary embodiment, the liquid store is configured as a removable and disposable capsule and wherein the main body further comprises a capsule seating configured to receive replaceable capsules comprising a liquid store.

According to an exemplary embodiment, the liquid store is refillable.

BRIEF DESCRIPTION OF THE DRAWINGS

The invention will now be described with reference to the appended drawings, which by way of example illustrate embodiments of the present invention and in which like features are denoted with the same reference numerals, and wherein.

DETAILED DESCRIPTION

As used herein, the term "inhaler" or "electronic cigarette" may include an electronic cigarette configured to deliver an aerosol to a user, including an aerosol for smoking. An aerosol for smoking may refer to an aerosol with particle sizes of 0.5-7 microns. The particle size may be less than 10 or 7 microns. The electronic cigarette may be portable.

Figure 1C:
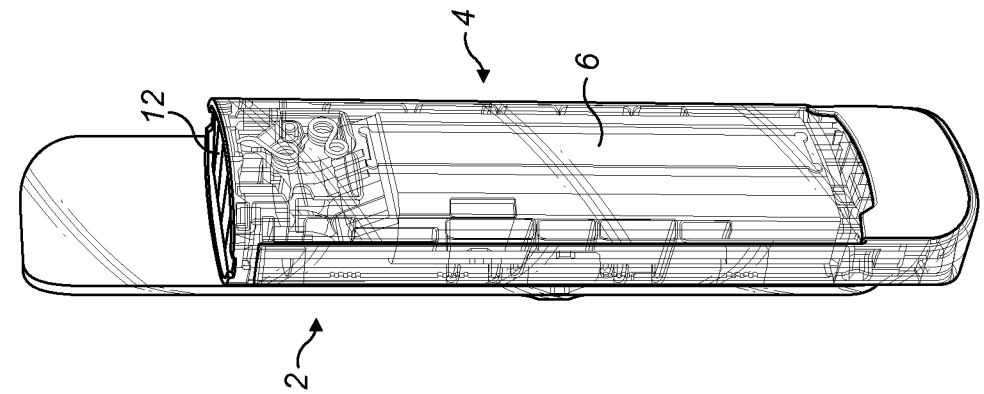
FIG. 1c is a schematic perspective view of the inhaler in FIGS. 1a and 1b, wherein the back panel of the inhaler has been removed.
Figure 1B:
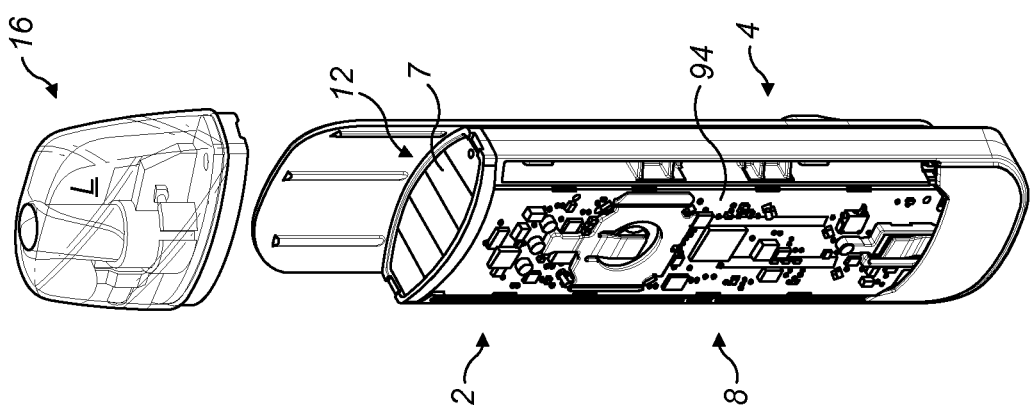
FIG. 1b is a schematic perspective view of the inhaler and capsule of FIG. 1a and in which the front panel of the inhaler has been removed.
Figure 1A:
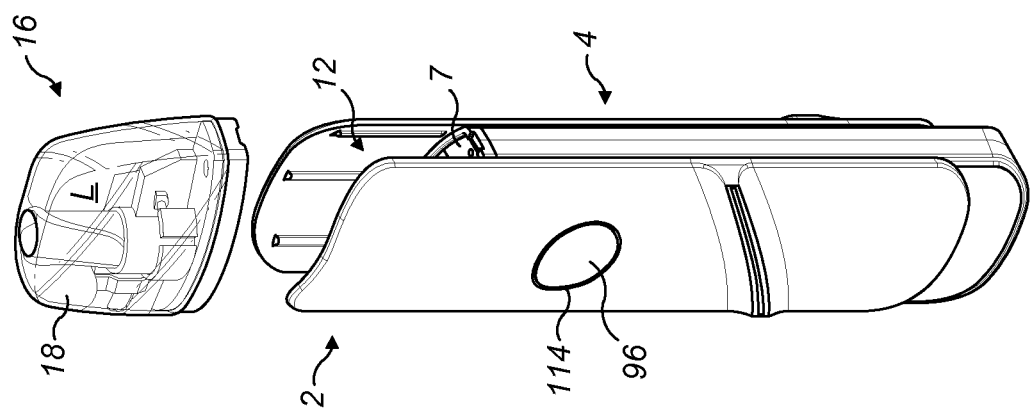
FIG. 1a is a schematic perspective view of an inhaler and a capsule according to an exemplary embodiment of the present invention.

Referring to the drawings and in particular to FIGS. 1a to 1c, an electronic cigarette 2 for vaporizing a liquid L is illustrated. The electronic cigarette 2 can be used as a substitute for a conventional cigarette. The electronic cigarette 2 has an elongate main body 4 comprising a power supply unit 6, electrical circuitry 8 and a seating 12 for a liquid reservoir 32 in the form of a removable capsule 16. The electrical circuitry 8 may advantageously be arranged on a printed circuit board (PCB) 94. In a non-illustrated embodiment, the capsule seating 12 can be configured to permanently hold a refillable liquid reservoir 32 in the form of a refillable tank. However in the embodiments illustrated in the appended figures, the capsule seating 12 is advantageously configured to receive disposable capsules 16 comprising a vaporizing liquid L. The vaporizing liquid L can comprise propylene glycol or glycerin, which is able to produce a visible vapor. The vaporizing liquid L may further comprise other substances such as nicotine and flavorings The capsule seating 12 is in the form of a cavity configured to receive the capsule 16. The capsule seating 12 is provided with a connection portion 7 configured to hold the capsule 16 firmly to the capsule seating 12. The connection portion 7 could for instance be an interference fit, a snap fit, a screw fit, a bayoneted fit or a magnetic fit. The capsule seating 12 further comprises a pair of electrical connectors (not shown) configured to engage with corresponding power terminals on the capsule 16 in order to provide power to heat up the liquid L in the capsule 16.

Figure 2A:
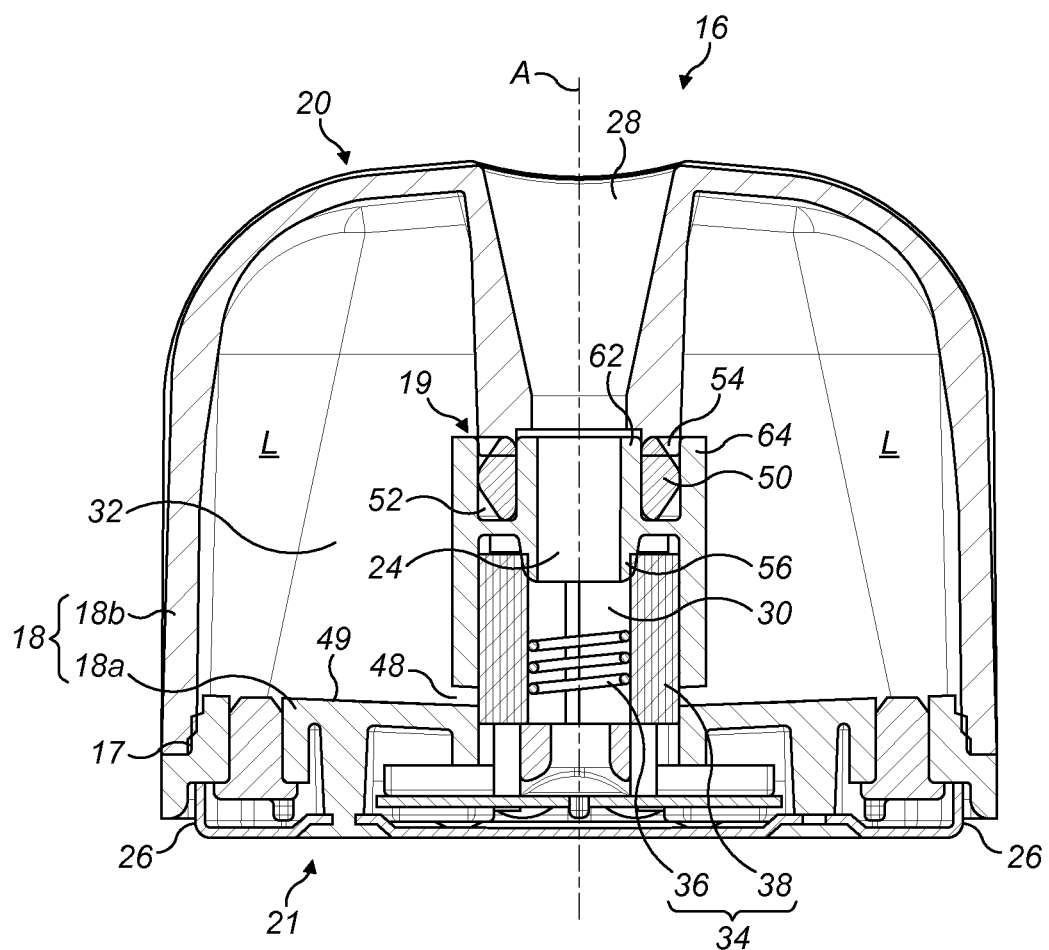
FIG. 2a is a schematic front cross-sectional view of a capsule according to an embodiment of the present invention.
Figure 2B:
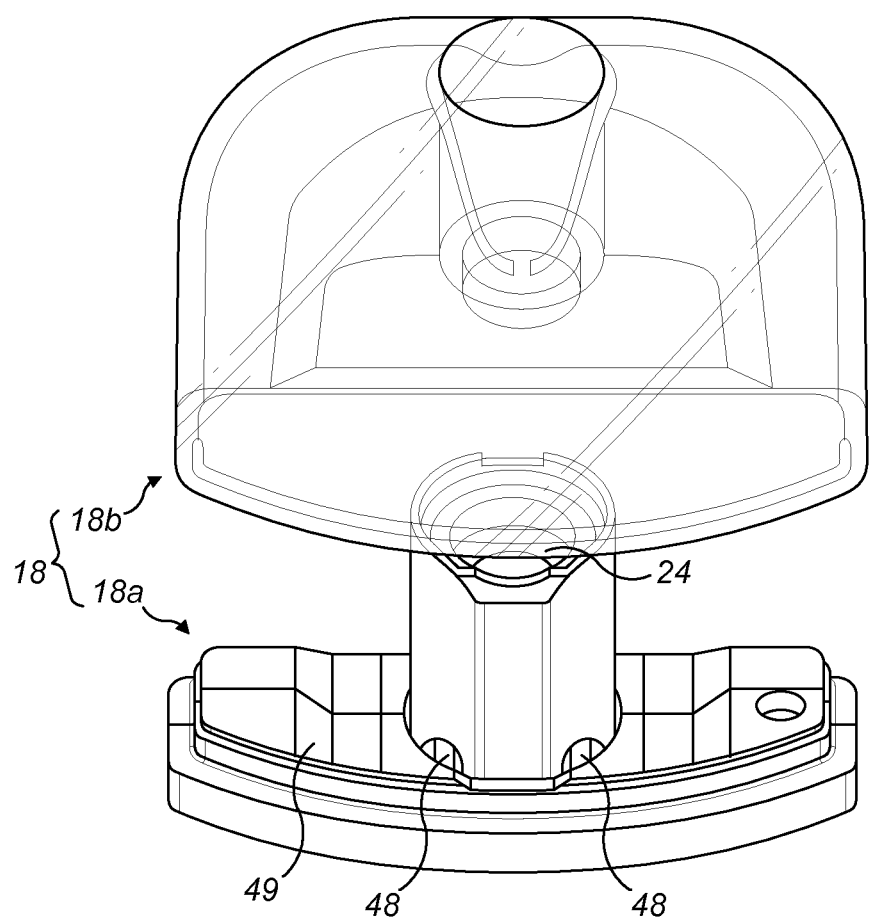
FIG. 2b is a perspective view of a capsule separated into inner and outer housings.

A capsule 16 according to a preferred embodiment of the present invention is illustrated in FIGS. 2a and 2b, the capsule 16 comprises a housing 18, a liquid reservoir 32, a vaporizing unit 34 and power terminals (not shown). The housing 18 has a mouthpiece portion 20 provided with a vapor outlet 28. The mouthpiece portion 20 may have a tip-shaped form to correspond to the ergonomics of the user's mouth. On the opposite side of mouthpiece portion 20, a capsule connection portion 21 is located. The capsule connection portion 21 is configured to connect with the connection portion 7 in the capsule seating 12. In the illustrated embodiment of FIGS. 2a and 2b, the connection portion 21 on the capsule 16 is a magnet or a metallic plate, configured to connect to a magnetic surface in the connection portion 7 of the capsule seating 12. The capsule housing 18 may be formed with a transparent material, whereby the liquid level of the capsule 16 is clearly visible to the user. The housing 18 may be formed with a polymeric or plastic material, such as polyester.

The vaporizing unit 34 comprises a heating element 36 and a fluid transfer element 38. The fluid transfer element 38 is configured to transfer the liquid L by capillary action from the liquid reservoir 32 to the heating element 36. The fluid transfer element 38 can be a fibrous or porous element such as a wick made from twined cotton, silica or a porous ceramic material. Alternatively, the fluid transfer element 38 can be any other suitable porous element.

As seen in FIGS. 3a to 3c, 4a and 4b, the electronic cigarette 2 further comprises a protective cover system 59. The protective cover system 59 comprises at least one panel 60 slidably attached to the elongate main body 4 and configured to move in the longitudinal direction of the electronic cigarette 2. The panel 60 is movable between an extended position and a retracted position.

Figure 3A:
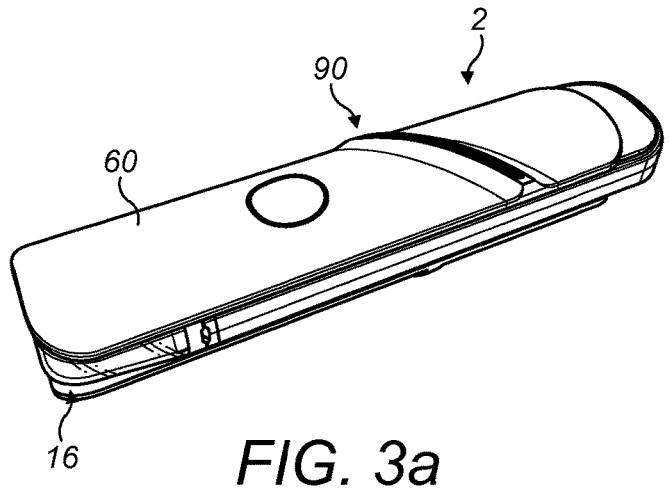
FIG. 3a is schematic perspective view of an inhaler of the present invention with a panel in an extended position so that the capsule is covered.
Figure 3B:
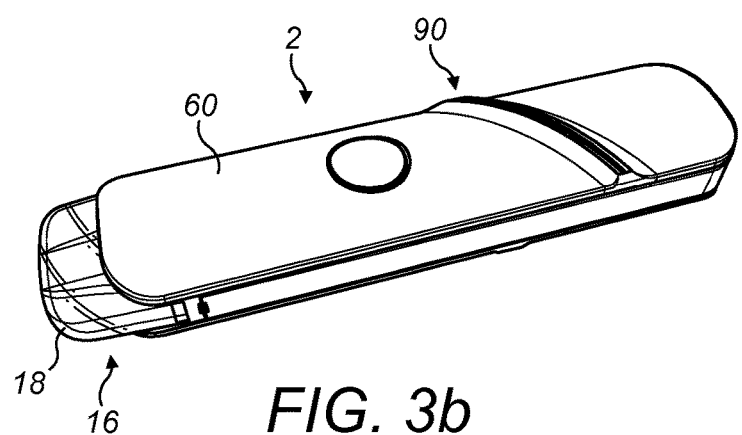
FIG. 3b is schematic perspective view of an inhaler of the present invention with a panel in a retracted position so that the capsule is exposed.

In the retracted position as illustrated in FIG. 3b, the capsule 16 is exposed so at least the mouthpiece portion 20 of the capsule 16 is exposed. The mouthpiece portion 20 needs to be exposed during use of the electronic cigarette 2 in order to produce a comfortable contact surface for the user's mouth.

In the extended position as illustrated in FIG. 3a, the panel 60 extends completely or at least partially over the capsule 16. The extended panel 60 protects the capsule 16 from being dislodged from the capsule seating 12. Additionally, the panel 60 in the extended position protects the capsule 16 from debris.

A pair of rail members 62 are connected to the elongate main body 4. The rail members 62 can be elongate rods. The rods 62 can be made from a metallic material such as stainless steel. The end portions 65 of the rail members 62 are connected to the elongate main body 4. The panel 60 comprises connectors 64 configured to attach to the rail members 62, so that the panel 60 can move along the longitudinal direction of the rail members 62.

Figure 5A:
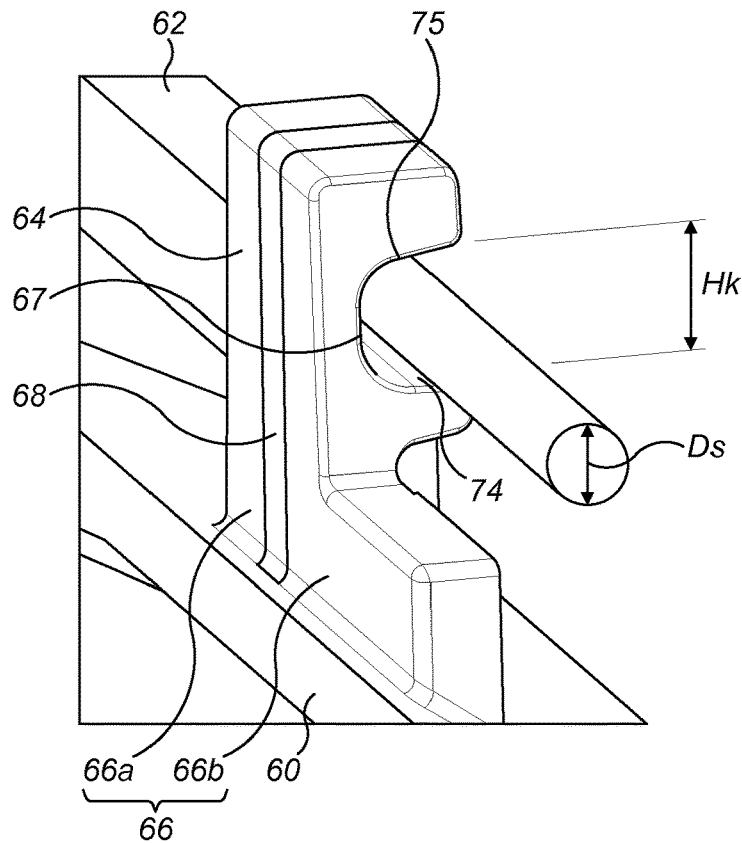
FIGS. 5a to 5c are schematic perspective views and cross-sectional views of the details of the connection between the panel connectors and the slide rails.
Figure 5B:
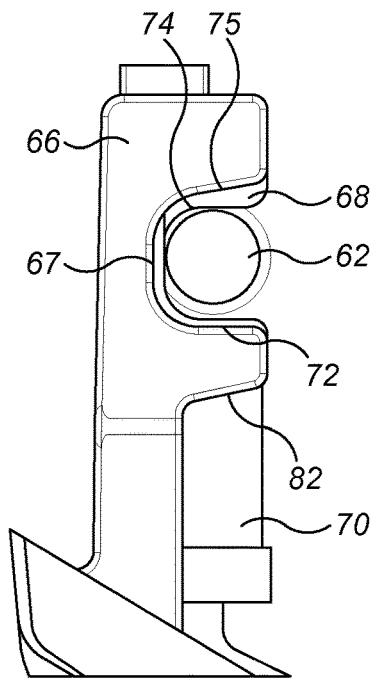
Figure 5C:
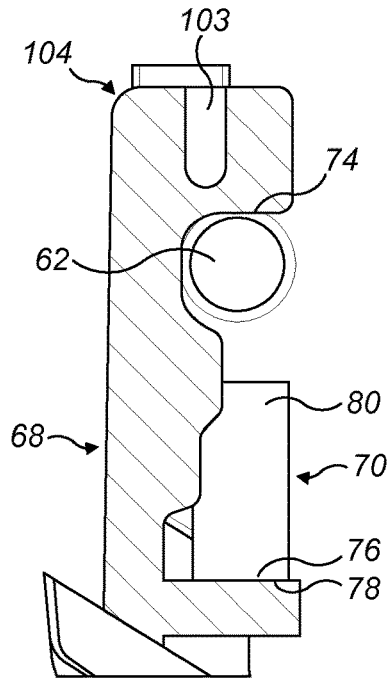

The details of the connectors 64 are further illustrated in FIGS. 5a to 5c. The connectors 64 are provided with keyways 67 configured to receive the rail members 62. The connectors 64 also have some freedom of movement in a direction transverse to the longitudinal direction of the elongate main body 4. This enables the panel 60 to move over imperfections on the rail members 62 or in the main body 4. The transverse direction substantially corresponds to the direction of a normal vector from the panel 60; a direction that is perpendicular to the longitudinal axis of the rail members 62.

The connector 64 comprises a fixed portion 66 and a movable portion 68. The keyway 67 comprises a first contact surface 72 and a second contact surface 74, wherein the first contact surface 72 is located on the fixed portion 66 and the second contact surface 74 is located on the movable portion 68. The fixed portion 66 is fixedly attached to the panel 60. The fixed portion 66 can advantageously be formed as an integrated part together with the panel 60. For instance, the panel 60 and the fixed portion 66 can be formed in an injection-molding or ultrasonic welding process. The fixed portion 66 comprises a first protruding portion 66a and a second protruding portion 66b. The movable portion 68 can be located in-between the first protruding portion 66a and the second protruding portion 66b.

As best seen in FIG. 5c, the movable portion 68 is connected to the fixed portion 66 using an elongate protrusion 103 that can move within a corresponding groove in the fixed portion 66. The movable portion 68 fits loosely between the first protruding portion 66a and the second protruding portion 66b so that it can slide in a direction defined by the main axis of the elongate protrusion 103— that is a direction that is perpendicular to the longitudinal axis of the rail member 62 and is parallel to a surface normal vector on the panel 60.

The movable portion 68 comprises a rigid portion 104 and a resilient member 70. The fixed portion 66 is configured to provide the first contact surface 72 for the rail member 62. The rigid portion 104 of the movable portion 68 is configured to provide the second contact surface 74 for the rail member 62. The first contact surface 72 and the second contact surface 74 are preferably formed from a low-friction material. The low-friction material can be e.g. Nylon, Polyester or Teflon.

The resilient member 70 has a first end 76 attached to a bottom surface 78 of the rigid portion 104, and a second end 80 abutting against a surface 82 of the fixed portion 66. This enables the resilient member 70 to provide a suspension effect to the second contact surface 74 in the keyway 67 for the rail member 62. The biasing effect is thus achieved in the transverse direction of the panel 60. This enables the panel 60 to move smoothly over imperfections and at the same time avoid any rattling sound from the level of play accorded between the panel 60 and the main elongate body 4.

The resilient portion 70 can be a biasing member, such as a compression spring. In an advantageous embodiment, the resilient portion 70 is a plug of resilient material. The use of a resilient material is advantageous as it provides a simple design, which is easy to manufacture. The connection between the resilient material 70 and the movable portion 68 can easily and durably be achieved by a thermoplastic joint or an adhesive. The resilient material can be a resilient foam polyurethane or polyethylene.

As seen in FIG. 5a, a level of play, or freedom, of the panel 60 is needed in the transverse direction in order to allow the panel 60 to move in the transverse direction. The level of play in relation to the elongate main body 4 is defined from the height $H_k$ of the keyway 67 and measured between the second contact surface 74 and the top contact surface 75 of the fixed portion 66. The slide rail 62 is provided with a diameter $D_s$. Consequently, the level of play in the transverse direction of the panel 60 is defined as $H_k$-$D_s$. The level of play is advantageously in the range of between 0.05 and 1 mm.

In this way, the movable portion 68 in FIGS. 5a to 5c is provided between the first protruding portion 66a and the second protruding portion 66b of the fixed portion 66. The rail member 62 is held lightly in compression between the first contact surface 72 on the fixed portion 66 and the second contact surface 74 on the movable portion 68. This is achieved by virtue of the resilient portion 70 which exerts a force on the rigid portion 104 of the movable portion 68 so that it is held in tension and the second contact surface 74 is urged towards the rail member 62. This allows the connector 64 to slide smoothly relative to the rail member 62 in the longitudinal direction, with the rail member 62 being loosely squeezed between the first and second contact surfaces 72, 74.

The position of the rail member 62 within the keyway 67 can be changed in the transverse direction. This provides a suspension effect so that the panel 60 can move slightly towards or away from the elongate body 4. The resilient portion 70 is compressible, and compression of the resilient portion 70 causes the second contact surface 74 to move in the transverse direction within the keyway 67. This can change the distance between the first contact surface 72 and the second contact surface 74. In particular, it can cause the second contact surface 74 to retract within the keyway 67. This can increase the distance between the first contact surface 72 and the second contact surface 74. In fact, when the resilient portion 70 is compressed it is possible that only the second contact surface 74 will actually be in contact with the rail member 62. A gap may therefore be created between the first contact surface 72 and the rail member 62.

In the present embodiment the first contact surface 72 is fixed in position in the keyway 67 and the second contact surface 74 is movable in the transverse direction. In other embodiments it may be possible for both contact surfaces 72, 74 to be movable in the transverse direction in order to provide the desired suspension between the rail members 62 and the connectors 64. In this design the movable portion 68 may provide the first contact surface 72 and the second contact surface 74. A restoring force is preferably provided by the resilient portion 70 so that a stable position is provided with the rail member 62 supported at a central position within the keyway 67. In this way, the rail 62 may be suspended flexibly in the transverse direction, within the keyway 67.

As best seen in FIGS. 4a and 3a to 3c, the electronic cigarette 2 may comprise a first slideable panel 60a and a second slideable panel 60b. The first slideable panel 60a and the second slideable panel 60b are configured to move in unison.

Figure 3C:
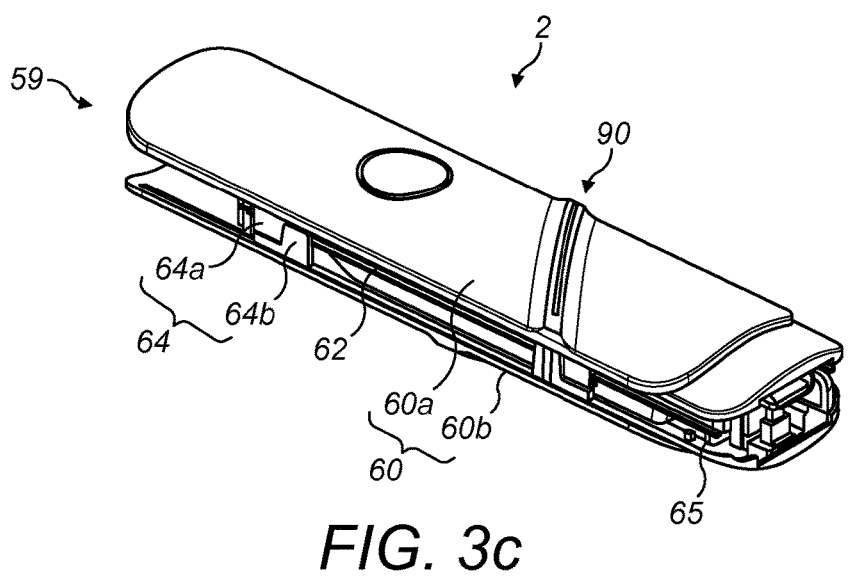
FIG. 3c is a schematic perspective view of the inhaler of FIGS. 3a and 3b, in which the side panel has been removed such that the slide rails and connectors are visible.

As best seen in FIG. 3c, the first panel 60a and the second panel 60b are both provided with connectors 64 configured to attach to the slide rails 60 as previously described. The connector 64a of the first sliding panel 60a is abutting the connector 64b of the second sliding panel 60b, which enables the panels 60a and 60b to be operationally connected to each other. The first panel 60a may be configured as a front panel and the second panel 60b can be configured as a back panel 60b. The first panel advantageously comprises a user-interface 90.

In the present embodiment, the rail members 62 are provided on the elongate body 4 and connectors 64 are provided on the panel 60. In a different embodiment, a similar effect may be provided with connectors on the elongate body and rail members on the panel 60. As an alternative to rail members it may be possible to provide a guide member such as a slot or keyway in which a connector can slide.

As seen in FIG. 4b and FIGS. 7a to 7c, the first panel 60a and second panel 60b may further comprise a biasing element 102 configured to render the first panel 60a and second panel 60b bi-stable between the extended position and the retracted position. It is advantageous to provide a bi-stable movement to ensure that the panel is either positioned in an operative position or a closed position and not somewhere in-between. The bi-stable biasing member 102 is located on the main body 4 and connected to the panel via a protrusion 105.

Figure 4B:
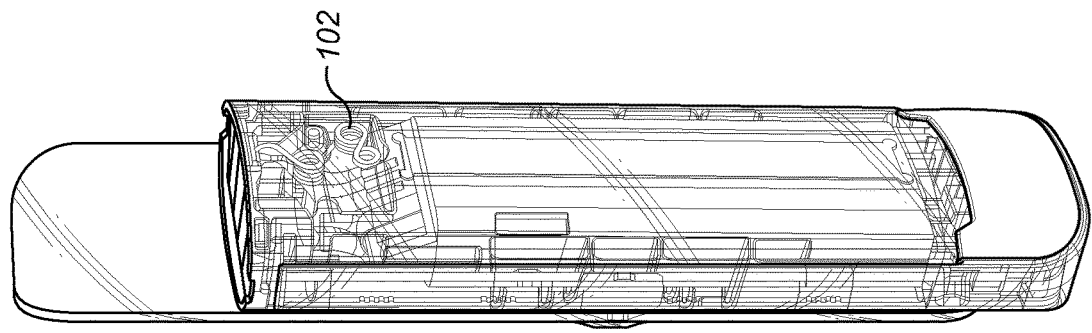
FIG. 4b is a schematic view of the inhaler of FIG. 4a with the back panel removed.
Figure 4A:
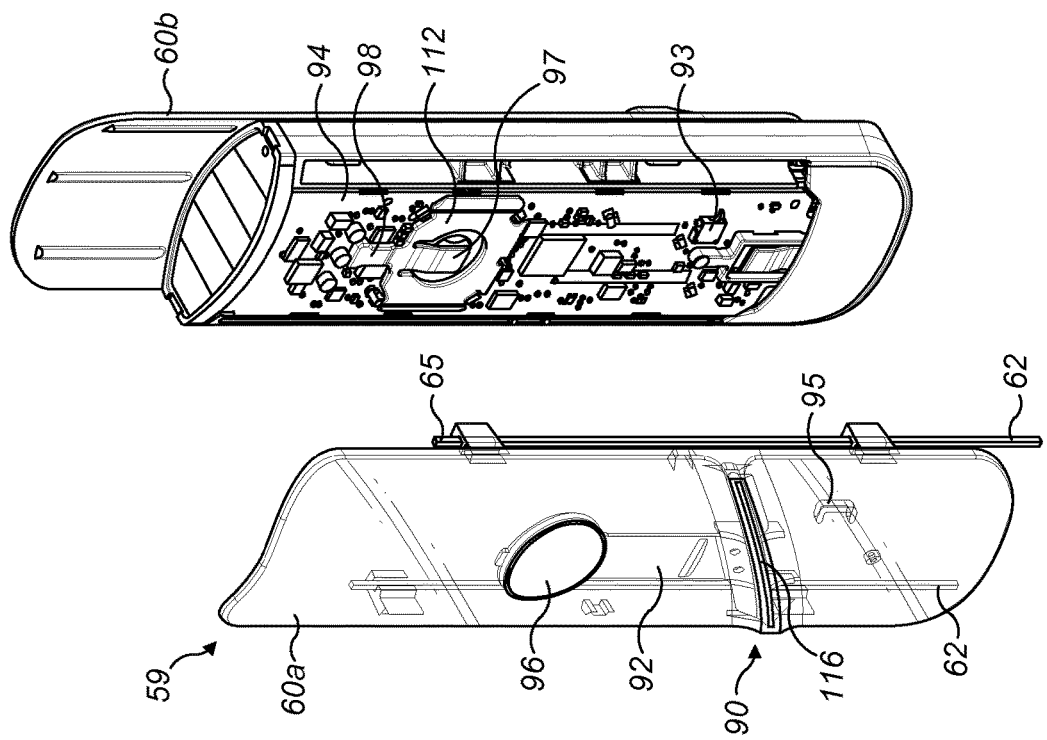
FIG. 4a is a schematic exploded view of the inhaler of FIGS. 3a to 3c.

As seen in FIG. 4a, the elongate main body 4 may comprise an electronic switch 93 configured to activate the electrical circuitry of the electronic cigarette 2. The switch may be fixedly attached to a printed circuit board 94, which is housing the electrical circuits. As the front panel 60a may be operatively connected to the electrical circuit, the correct position of the front panel 60a in relation to the elongate main body 4 is needed.

The front panel 60a may therefore further comprise an engagement element 95 configured to physically move the switch 93. The switch 93 is only activated when the engagement element 95 is aligned with the switch 93, which corresponds to the retracted position of the panel 60. In another embodiment a different switching or button mechanism could be used. In one example a magnet could be provided on the panel 60 and a reed switch could be provided on the PCB 94. The front panel 60a is advantageously provided with an activation button 96 for the heating element 36.

As the front panel 60a is configured to move in relation to the PCB 94 and the activation circuit, it is desirable to protect the PCB 94 when the panel 60a is in the extended position. The main body 4 may therefore be provided with an abutment portion 98 to protect the PCB 94 from the activation button 96 when the panel 60a is in an extended position. The electronic cigarette 2 according to the present invention can have several activation mechanisms or push buttons, wherefore the PCB may comprise several abutment portions 98 configured to support each activation button 96 when the panel 60a is in the extended position.

The front panel may further comprise an interface in the form of a display 90 configured to display information such as level of battery power, heating profiles, estimated consumed amount of vapor (or nicotine) operating mode, connectivity status, child lock etc. As the present electronic cigarette 2 can be a small and light device configured to be held comfortably by a user but at the same time allows for a plurality of technical functionalities, the display 90 needs to be versatile and configured to display different types of information. The panel 60a may optionally be provided with fixed indicators (e.g. printed or engraved) symbols and text next to the sections. The indicators further help the user to distinguish different information on the display.

Figure 6:
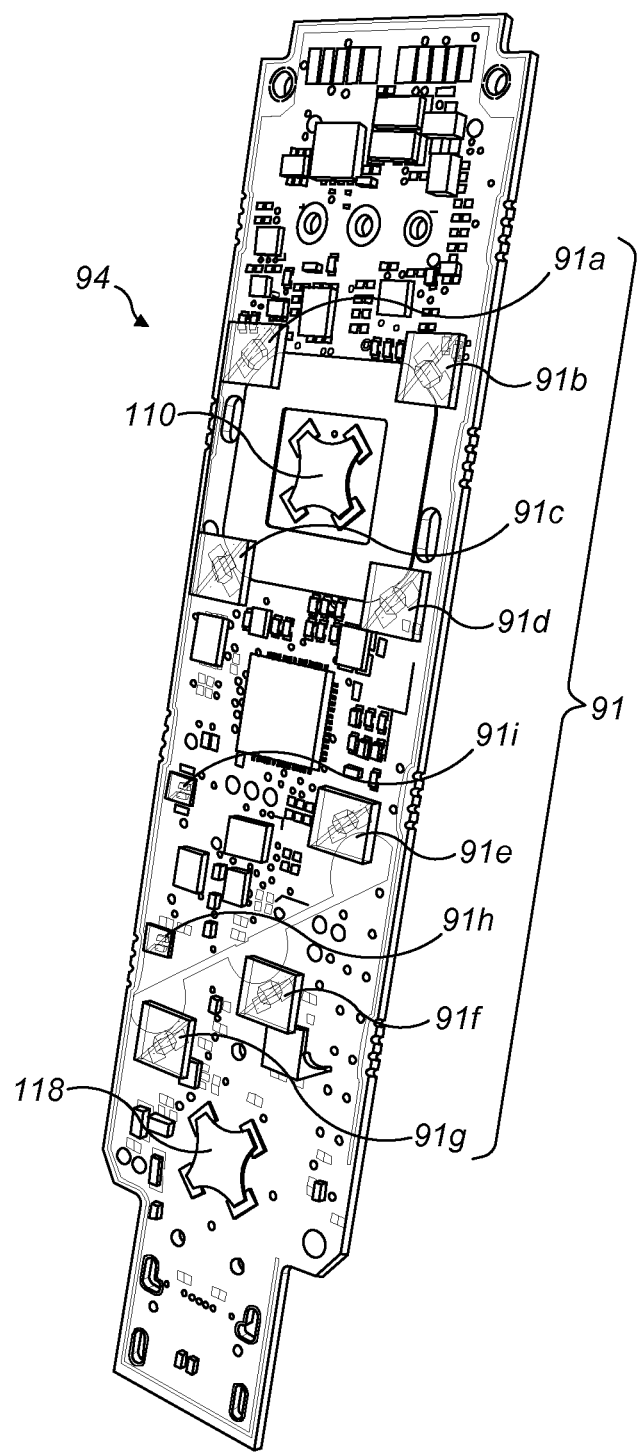
FIG. 6 is a schematic perspective view of a PCB according to the present invention.
Figure 7C:
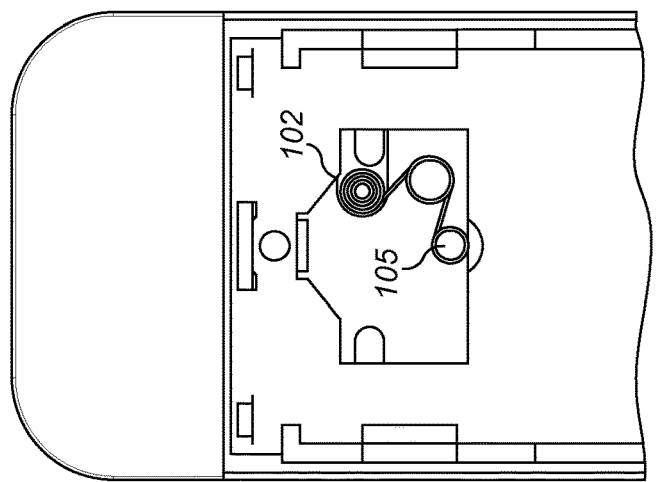
FIGS. 7a to 7c are schematic perspective views of a bi-stable mechanism of the slideable panel according to an embodiment of the present invention.
Figure 7B:
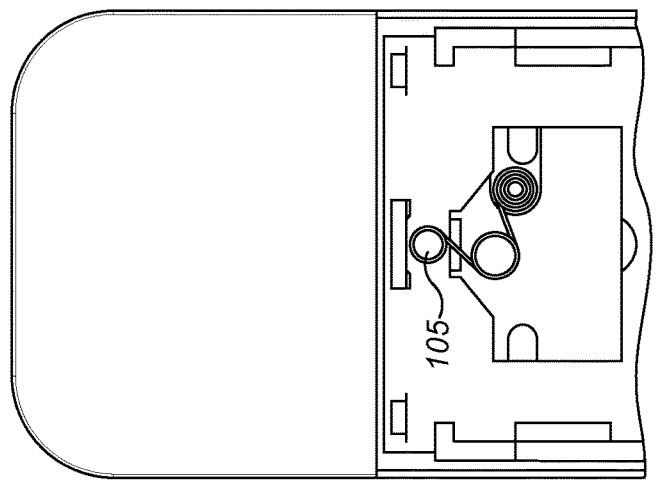
Figure 7A:
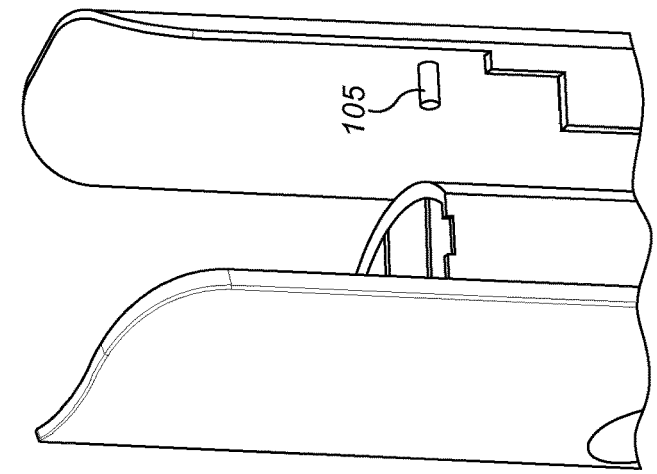

As seen in FIG. 6, a plurality of light sources 91a to 91i are operationally coupled to the display 90. Each light source 91 can be a RGB LED or a plurality of different colored LEDs. The light sources 91 are electrically connected to the PCB 94. Grouping the light sources 91 on the PCB 94 simplifies and facilitates the manufacturing of the electronic cigarette 2. The present display 90 can be located on the slideable panel 60.

The light sources 91 can be located in direct proximity to the display 90. Alternatively, the light sources 91 can be located at a distance of the display 90. The light from the light sources 91 can be transferred to the display by using a light guide 92.

A group of LEDs 91a, 91b, 91c, 91d are provided on the PCB 94 at the vertices of a square that surrounds a first switch 110. A first light diffusing element 112 is positioned between the PCB 94 and the slideable panel 60. The first light diffusing element 112 is configured to receive light from the LEDs 91a, 91b, 91c, 91d and diffuse it so that a halo effect can be created around the button 96 when the slideable panel is in the retracted position. The first light diffusing element 112 is translucent and diffuses the light from the four individual LEDs so that a ring light effect is created and the underlying LEDs are not individually visible. A transparent ring 114 is provided around the button 96 in the slideable panel 60 through which the first light diffusing element 112 is visible, at least when the slideable panel 60 in the retracted position.

The button 96 in the slideable panel 60 can be depressed to actuate the first switch 110 when the panel 60 is in the retracted position The button 96 may have a contact surface configured to contact a lever 97 in the main body 4. The lever 97 closes and thus activates circuit to supply power to the heater when the button 96 is depressed. In an advantageous embodiment, the lever 97 is formed as an integral piece with the light guide 112.

In the extended position the button 96 is moved to a position where it overlies the abutment portion 98. The abutment portion 98 is provided at a raised position relative to the PCB 94, corresponding to the open position of the first switch 110. However, unlike the first switch 110 which is movable, the abutment portion 98 is fixed in position relative to the PCB 94. The abutment portion 98 therefore inhibits movement of the button 96 towards the PCB 94 when the slideable panel 60 is in the extended position. This can advantageously protect the PCB 94 from potential damage by the user depressing the button 96 when it is displaced from the first switch 110. In this example the abutment portion 98 is formed as part of the first light diffusing element 112. This is just one example of a technique for locking movement of the button 96 when the panel 60 is in the extended position.

The display 90 in the slideable panel 60 may include an angled slot that is a window through which light from LEDs 91e, 91f, 91g, 91h, 91i is viewable. The window includes a second light diffusing element 116. The second light diffusing element 116 is divided into three sections by optically opaque partitions (not shown). Each of the sections is arranged to overlie one of the LEDs 91e, 91f, 91g on the PCB 94 to couple light from the relevant LED for viewing by the user when the slideable panel 60 is in the retracted position. The second light diffusing element 116 also overlies LED 91h in the retracted position.

In the extended position the slideable panel 60 is moved relative to the PCB 94 so that the second light diffusing element 116 in the angled slot no longer overlies the LEDs 91e, 91f, 91g, 91h. In this position these LEDs 91e, 91f, 91g are obscured by the opaque surface of the slideable panel 60 and are rendered invisible to a user. In the extended position the second light diffusing element 116 in the angled slot is arranged to overlie the LED 91i. Thus, in this embodiment, only one LED 91i is viewable through the angled slot when the slideable panel 60 is in the extended position.

A second switch 118 is provided on the PCB 94. The LEDs 91e, 91f, 91g, 91h, 91i are provided at positions on the PCB 94 between the first switch 110 and the second switch 118. The second switch 118 can be activated by depression of the lower half of the slideable panel 60 relative to the PCB 94. This is enabled by the suspension effect described above that allows the panel 60 to be moved in a transverse direction, towards the elongate body 4.

The light sources 91h, 91i may be provided to indicate remaining battery power in the device. Each light source 91h, 91i can actually include two separate LEDs with different colours, such as green and red. The relative amount of light emitted by the respective LED colours may be indicative of the amount of battery power remaining. The LEDs 91i, 91h are visible in the extended and retracted positions of the slideable panel 60 respectively, and this can allow remaining battery power to be analysed when the device is operative and inoperative. In alternative arrangements the LEDs 91h, 91i may be used to indicate a variety of other metrics related to the device including whether the electronic cigarette is connected to an external device such as a charger via a socket or whether the electronic cigarette is wirelessly connected to an external device such as a smartphone (for example using Bluetooth). The LEDs 91h, 91i may be pulsed and the pulse frequency may be used to indicate different types of information both when the slideable panel 60 is retracted and when it is extended. As explained above, an engagement element 95 on the slideable panel 60 is configured to physically move the switch 93 when it moves from the retracted position to the extended position and vice-versa. This switch 93 may be used to control which of the LEDs 91h, 91i is operated, depending on whether the panel 60 is in the extended or retracted position.

In this embodiment the LEDs 91e, 91f, 91g, 91h are rendered invisible from a user's perspective by movement of the panel 60 from the retracted position to the extended position. In another embodiment the LEDs 91e, 91f, 91g, 91h could be rendered inactive when the engagement element 95 on the slideable panel 60 physically moves the switch 93 when it moves from the retracted position to the extended position. The light sources 91 could even be provided on a surface of the slideable panel 60, rather than the PCB 94, and may be rendered active or inactive by the engagement element 95 and the switch 93.

The LEDs 91e, 91f, 91g and the LEDs 91a, 91b, 91c, 91d can be activated and visible only when the slideable panel 60 is in the retracted position, ready for use. These light sources may be used to indicate sensed information relating to the capsule 16 including authentication information, expiry date and chemical composition (e.g. nicotine content). The LEDs may also be used to indicate total estimated consumption, duration of utilization, remaining battery power or capsule information.

The skilled person will realize that the present invention by no means is limited to the described exemplary embodiments. The mere fact that certain measures are recited in mutually different dependent claims does not indicate that a combination of these measures cannot be used to advantage. Moreover, the expression "comprising" does not exclude other elements or steps. Other non-limiting expressions include that "a" or "an" does not exclude a plurality and that a single unit may fulfill the functions of several means. Any reference signs in the claims should not be construed as limiting the scope. Finally, while the invention has been illustrated in detail in the drawings and in the foregoing description, such illustration and description is considered illustrative or exemplary and not restrictive; the invention is not limited to the disclosed embodiments.

The invention claimed is:
1. An electronic cigarette device comprising:
   an elongate main body configured to house a liquid reservoir,
   at least one slideable panel connected to the elongate main body and moveable in relation to the elongate main body in a longitudinal direction of the elongate main body between an extended position and a retracted position, whereby the liquid reservoir is exposed or more exposed when the at least one slideable panel is in the retracted position, wherein one of the elongate main body and the at least one slideable panel comprises at least one guide member and the other of the elongate main body and the at least one slideable panel comprises at least one connector configured to connect to the at least one guide member, and wherein the at least one connector is connected to the at least one guide member such that the at least one slideable panel is slideably moveable relative to the elongate main body in the longitudinal direction and is also movable in a transverse direction that is perpendicular to the longitudinal direction.

2. The electronic cigarette according to claim 1, wherein the elongate main body comprises the at least one guide member and the at least one slideable panel comprises the at least one connector.

3. The electronic cigarette according to claim 1, wherein the liquid reservoir is configured as a removable capsule provided with a mouthpiece portion.

4. The electronic cigarette according to claim 1, wherein the at least one connector is biased in the transverse direction.

5. The electronic cigarette according to claim 1, wherein the at least one connector comprises a fixed portion fixedly attached to the at least one slideable panel and a moveable portion that is movable in relation to the fixed portion in the transverse direction.

6. The electronic cigarette according to claim 5, wherein the fixed portion comprises first and second protrusions, wherein the movable portion is slidably received between the first and second protrusions.

7. The electronic cigarette according to claim 6, wherein the at least one connector comprises a keyway configured to receive the at least one guide member.

8. The electronic cigarette according to claim 5, wherein the keyway comprises a first contact surface on one side of the at least one guide member and a second contact surface on another side of the at least one guide member, wherein at least one of the first contact surface and the second contact surface is biased towards the at least one guide member.

9. The electronic cigarette according to claim 5, wherein the at least one connector comprises a biasing member configured to bias the movable portion relative to the fixed portion.

10. The electronic cigarette according to claim 9, wherein the biasing member is a resilient material of spongy foam.

11. The electronic cigarette according to claim 1, wherein the at least one slideable panel is arranged to move at a distance of between 0.05 and 1 mm in the transverse direction of the elongate main body.

12. The electronic cigarette according to claim 1, wherein the at least one slideable panel comprises a first slideable panel, and the electronic cigarette further comprises a second slideable panel configured to move in unison with the first slideable panel.

13. The electronic cigarette according to claim 12, wherein the elongate main body comprises the at least one guide member and the first slideable panel comprises the at least one connector, and wherein the at least one connector of the first slideable panel is in abutment with at least one connector of the second slideable panel such that they move together.

14. The electronic cigarette according to claim 1, wherein the elongate main body comprises an electrical activation circuit and an actuator element,
wherein the at least one slideable panel comprises an engagement element configured to move the actuator element, whereby the electrical activation circuit is only activated when the at least one slideable panel is in the retracted position.

15. The electronic cigarette according to claim 14, wherein the at least one slideable panel further comprises a heating element activation button and wherein the heating element activation button is only operable when the at least one slideable panel is in the retracted position.

16. The electronic cigarette according to claim 15, wherein the electrical activation circuit is located on a printed circuit board, and wherein the elongate main body has at least one abutment portion configured to protect the printed circuit board from the heating element activation button when the at least one slideable panel is in an extended position.

17. The electronic cigarette according to claim 10, wherein the spongy foam is polyurethane or polyethylene.

18. The electronic cigarette according to claim 1, wherein the transverse direction is normal to the at least one slideable panel.

* * * * *